(12) United States Patent
Ogihara et al.

(10) Patent No.: US 7,959,596 B2
(45) Date of Patent: Jun. 14, 2011

(54) EXTRACORPOREAL CIRCUIT

(75) Inventors: Mitsuaki Ogihara, Shizuoka (JP);
Kazuhiko Takeuchi, Shizuoka (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 485 days.

(21) Appl. No.: 12/104,663

(22) Filed: Apr. 17, 2008

(65) Prior Publication Data

US 2008/0262405 A1 Oct. 23, 2008

Related U.S. Application Data

(60) Provisional application No. 60/946,197, filed on Jun. 26, 2007.

(30) Foreign Application Priority Data

Apr. 19, 2007 (JP) .................................. 2007-110651

(51) Int. Cl.
*A61M 19/00* (2006.01)
(52) U.S. Cl. ...................... 604/6.16; 604/6.01; 604/6.15
(58) Field of Classification Search ................. 604/4.01, 604/6.1, 6.11, 6.14, 6.15, 6.16; 210/645; 422/44, 45
See application file for complete search history.

(56) References Cited

U.S. PATENT DOCUMENTS

| 3,655,123 | A | * | 4/1972 | Judson et al. | 422/44 |
|---|---|---|---|---|---|
| 5,282,783 | A | * | 2/1994 | Lindsay | 604/6.09 |
| 6,454,736 | B1 | * | 9/2002 | Ludt et al. | 604/5.01 |
| 6,908,446 | B2 | | 6/2005 | Yokoyama et al. | |

FOREIGN PATENT DOCUMENTS

WO  WO 2006/047147 A1  5/2006

OTHER PUBLICATIONS

Extended European Search Report issued Jul. 29, 2009 by the European Patent Office in European Patent Application No. 09161639.1.
Communication Pursuant to Article 94(3) EPC issued Apr. 12, 2010 by the European Patent Office in European Patent Application No. 08 154 464.5.
Extended European Search Report issued in corresponding EP 08 15 4464.5, Jul. 18, 2008, EPO, Munich, DE.

(Continued)

*Primary Examiner* — Leslie R Deak
(74) *Attorney, Agent, or Firm* — Buchanan Ingersoll & Rooney PC

(57) ABSTRACT

An extracorporeal circuit, which makes it possible to efficiently collect priming solution by displacing the priming solution with blood after the priming solution is fed to the extracorporeal circuit to prime the extracorporeal circuit, includes a circuit body including first and second tubes, a feed bag that feeds the priming solution, a blood reservoir in which a liquid is temporarily stored, a third tube that branches out from the middle of the first tube, and a collection bag which communicates with the third tube and into which the priming solution is collected through the third tube. After the priming solution is fed from the feed bag to prime at least a housing, when the priming solution in the housing is displaced by blood, the priming solution in the housing is transferred and collected in the collection bag due to a height difference between the liquid level and the collection bag.

16 Claims, 13 Drawing Sheets

OTHER PUBLICATIONS

Rosengart, MD, Todd K., et al., "Retrograde Autologous Priming for Cardiopulmonary Bypass: A Safe and Effective Means of Decreasing Hemodilution and Transfusion Requirements," *The Journal of Thoracic and Cardiovascular Surgery*, Feb. 1, 1998, pp. 426-439, vol. 115, No. 2, Mosby-Year Book, Inc., St. Louis, MO, USA.

Eising, M.D., Gregory, P., et al., "Retrograde Autologous Priming: Is It Useful in Elective On-Pump Coronary Artery Bypass Surgery?", *Ann. Thorac. Surg.*, Jan. 2003, pp. 23-27, vol. 75, Issue 1, The Society of Thoracic Surgeons, Elsevier Science Inc.

Balachandran, Frca, Subramaniam, et al., "Retrograde Autologous Priming of the Cardipulmonary Bypass Circuit Reduces Blood Transfusion After Coronary Artery Surgery," *Ann. Thorac. Surg.*, Jun. 2002, pp. 1912-1918, vol. 73, Issue 6, The Society of Thoracic Surgeons, Elsevier Science Inc.

Cormack, CCP, John E., et al., "Hematocrit Prediction and Preservation for Cardiopulmonary Bypass," *E-Journal of Perfusion Technology*, Jun. 16, 2003, http://perfline.com/ejournal/2002/jec0102.html.

* cited by examiner

EXTRACORPOREAL CIRCUIT

This application claims priority under 35 U.S.C. §119(e) to U.S. Provisional Application No. 60/946,197 filed on Jun. 26, 2007, the entire content of which is incorporated herein by reference. This application is also based on and claims priority to Japanese Application No. 2007-110651 filed on Apr. 19, 2007, the entire content of which is incorporated herein.

BACKGROUND DISCUSSION

The present invention generally relates to a blood circulation system. More specifically, the invention pertains to an extracorporeal circuit.

TECHNOLOGICAL FIELD

U.S. Pat. No. 6,908,446 describes a known extracorporeal circuit that extracorporeally circulates blood. The extracorporeal circuit includes a venous line and an arterial line that are coupled to a patient, a blood reservoir connected on a downstream side of the venous line, an oxygenator connected on an upstream side of the arterial line, and a linkage line linking the blood reservoir and oxygenator.

When the extracorporeal circuit (hereinafter simply referred to as a circuit) described in this patent is used to extracorporeally circulate blood, a priming solution (for example, physiological saline) is fed to the circuit in order to prime the circuit. Thereafter, extracorporeal circulation is performed. When this kind of operation is performed, blood is diluted with the priming solution (hemodilution).

In recent years, a technique has been adopted prior to extracorporeal circulation involving collecting the priming solution as much as possible to hinder hemodilution. The technique is normally referred to as retrograde autologous priming (RAP). This RAP technique involves connecting to the circuit in advance a collection bag into which the priming solution is collected. In this state, blood is drawn from a patient to the circuit in a direction opposite to the direction of the normal flow of blood during extracorporeal circulation, and is used to thrust the priming solution in the circuit into the collection bag.

However, when the priming solution is merely thrust with regurgitant blood, the priming solution may not be fully collected in the collection bag, though it depends on the circuitry of the extracorporeal circuit. Therefore, as an auxiliary way for fully thrusting the priming solution, a pump may be adopted or an additional line may be included. This makes the circuitry complex. Consequently, manipulations to be performed on the circuit from the instant of priming to the instant of extracorporeal circulation (for example, starting or stopping of the pump and switching of lines in the circuit) become complex. Accordingly, it is difficult to quickly achieve the RAP, that is to quickly collect the priming solution.

SUMMARY

According to one aspect, an extracorporeal circuit for extracorporeally circulating blood comprises a circuit body for circulating liquid through a plurality of extracorporeal circuit components, the circuit body comprising a plurality of tube segments, a blood reservoir comprising one of the extracorporeal circuit components, the blood reservoir possessing an interiorly located storage chamber in which a liquid is received, a tube communicating with a first one of the tube segments, the tube possessing a lower end positioned in the storage space of the blood reservoir adjacent the bottom surface of the storage chamber, and a branch line branching out from an intermediate portion of the first tube segment. In addition, a collection container is provided and communicates with the branch line and into which liquid in the storage chamber flows by way of the branch line.

According to another aspect, an extracorporeal circuit for extracorporeally circulating blood comprises a circuit body comprised of a plurality of circuit tubes including a first circuit tube, wherein the first circuit tube is comprised of a plurality of tube segments including a first tube segment constituting a venous line adapted to be connected to a vein of a patient during extracorporeal circulation and a second tube segment constituting an arterial line adapted to be connected to an artery of the patient during extracorporeal circulation. The extracorporeal circuit also includes a blood reservoir connected to the first tube segment and having an interiorly located storage chamber for temporarily storing liquid, a pump connected to the reservoir and positioned along the circuit body to convey liquid in the circuit body, an oxygenator connected to the second tube segment and configured to perform gas exchange on blood flowing through the circuit body, and a priming solution feeding unit containing priming solution and in communication with the blood reservoir. A reservoir tube has one end communicating with the first tube segment constituting the venous line and an opposite end which is open and which is positioned adjacent a bottom of the storage chamber, while a branch line communicates with and branches out from an intermediate portion of the first tube segment constituting the venous line. The extracorporeal circuit also includes a collection container communicating with the branch line and into which the priming solution in the storage chamber is collected by way of the branch line. After the priming solution is fed from the priming solution feeding unit to the storage chamber to prime at least the storage chamber, the priming solution in the storage chamber is displaced by blood and is transferred to the collection container due to a difference in height of liquid in the storage chamber relative to liquid in the collection container.

According to a further aspect, a method of using an extracorporeal circuit comprises introducing a priming solution into an extracorporeal circuit to prime the extracorporeal circuit before introducing a patient's blood into the extracorporeal circuit, and with the introduction of the priming solution into the extracorporeal circuit introducing the priming solution into the interior of a blood reservoir constituting a part of the extracorporeal circuit. The extracorporeal circuit also comprises a circuit tube connected to the interior of the blood reservoir, a collection bag, and a branch line having one open end opening into the collection bag and an opposite end connected to and communicating with an intermediate portion of the circuit tube. The method further comprises positioning the collection bag relative to the blood reservoir so that the one open end is located elevationally lower than a level of the priming solution in the blood reservoir, and permitting the priming solution in the interior of the blood reservoir to flow into the collection bag by way of the branch line under a siphon principle.

BRIEF DESCRIPTION OF THE DRAWINGS

Features, characteristics and other aspects associated with the extracorporeal circuit here will become more apparent from the following detailed description considered with reference to the accompanying drawing figures briefly described below in which like elements are designated by like reference numerals.

DETAILED DESCRIPTION

Figure 11:
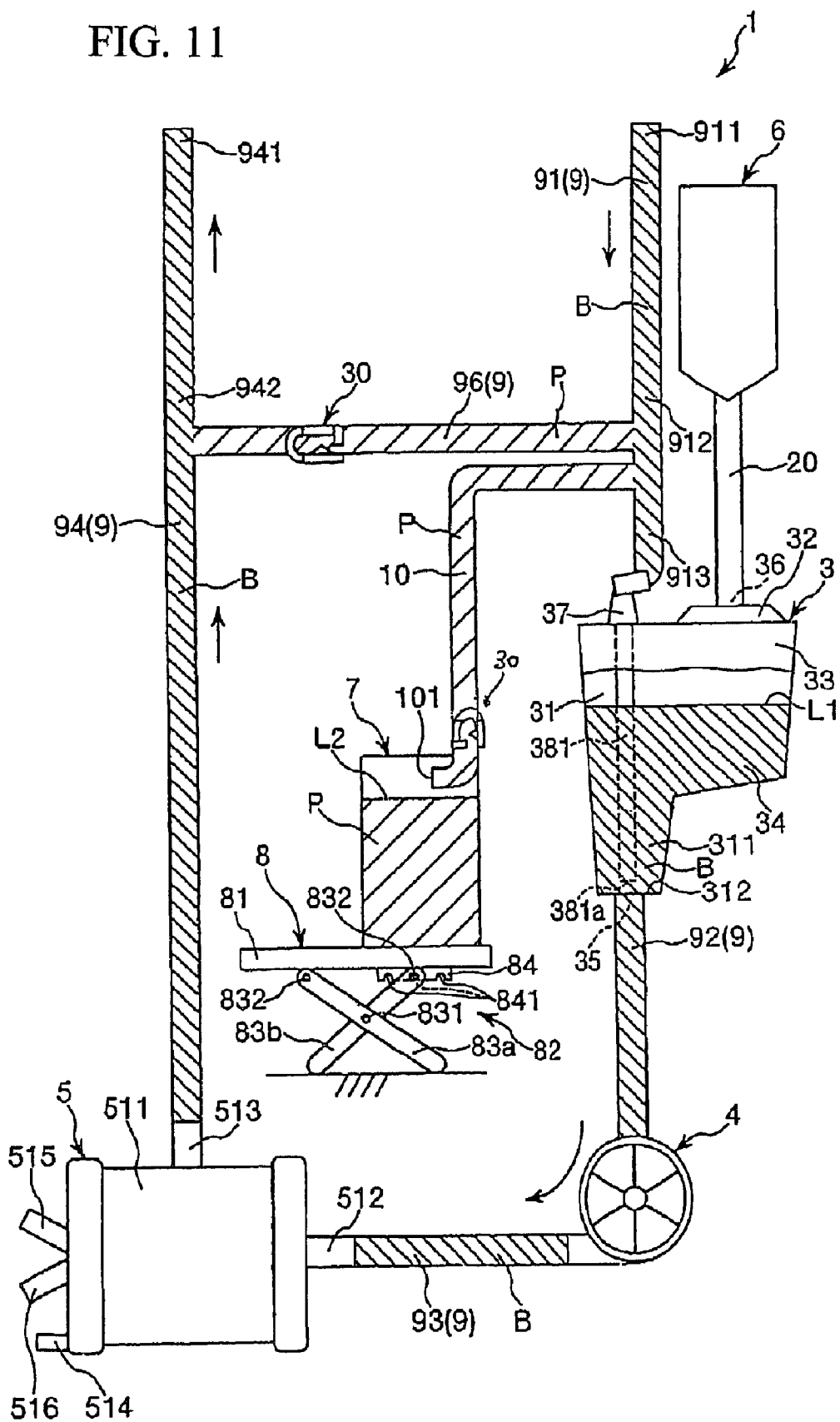
FIG. 11 is a schematic illustration of the circuitry of the extracorporeal circuit shown in FIG. 1, presenting another aspect of the sequential manner of use of the extracorporeal circuit.
Figure 12:
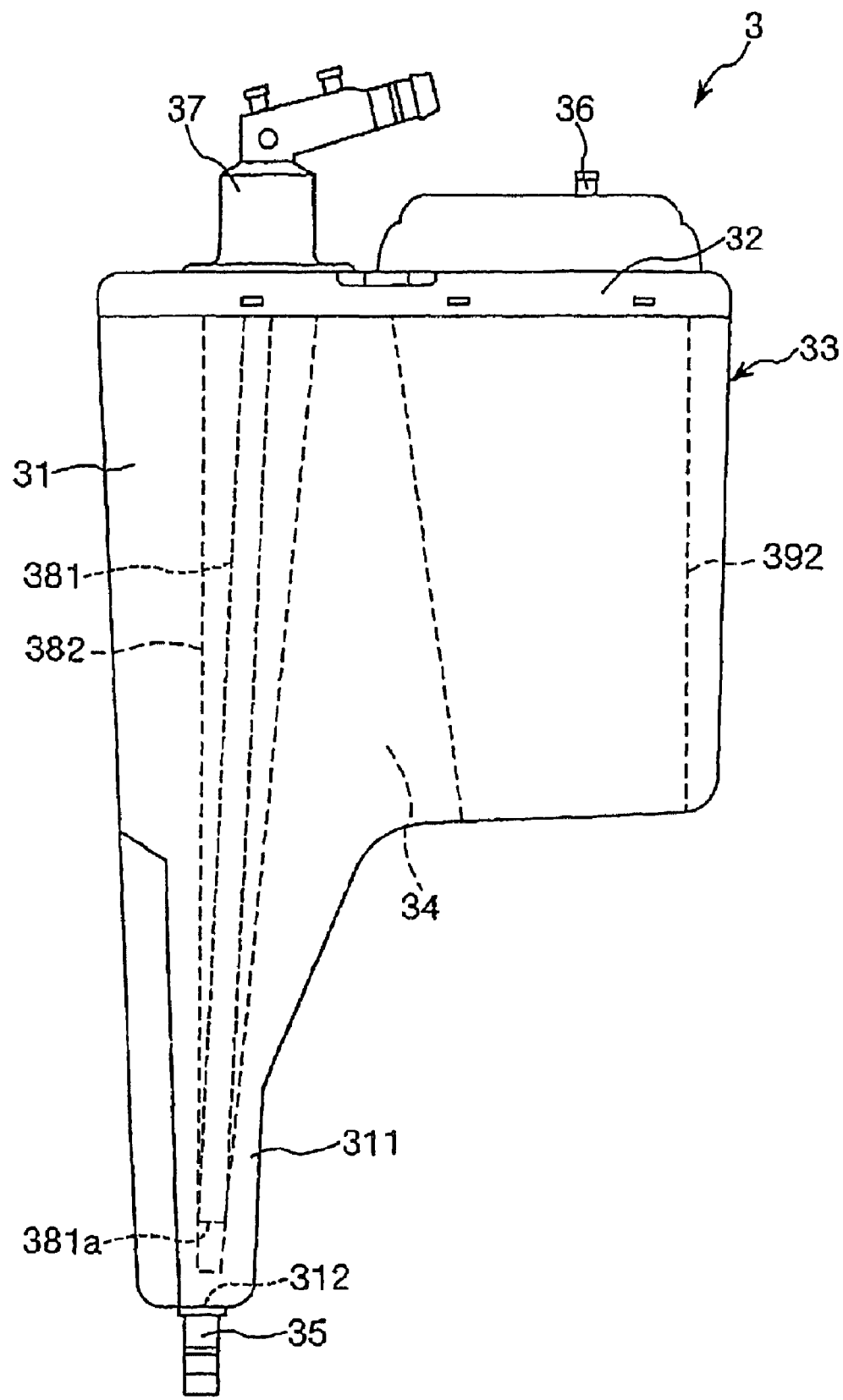
FIG. 12 shows the flank of a blood reservoir included in the extracorporeal circuit shown in FIG. 1.

FIGS. 1-11 illustrate a first embodiment of the circuitry of an extracorporeal circuit as disclosed herein. FIG. 12 is a side view of the blood reservoir included in the extracorporeal circuit shown in FIG. 1. For the sake of convenience, the part of the blood reservoir shown in the upper part of FIG. 12 is called the upper part of the blood reservoir and the part of the blood reservoir shown in the lower part of FIG. 12 is called the lower part of the blood reservoir. This same nomenclature also applies to the illustrations in FIG. 13 and FIG. 14.

Figure 1:
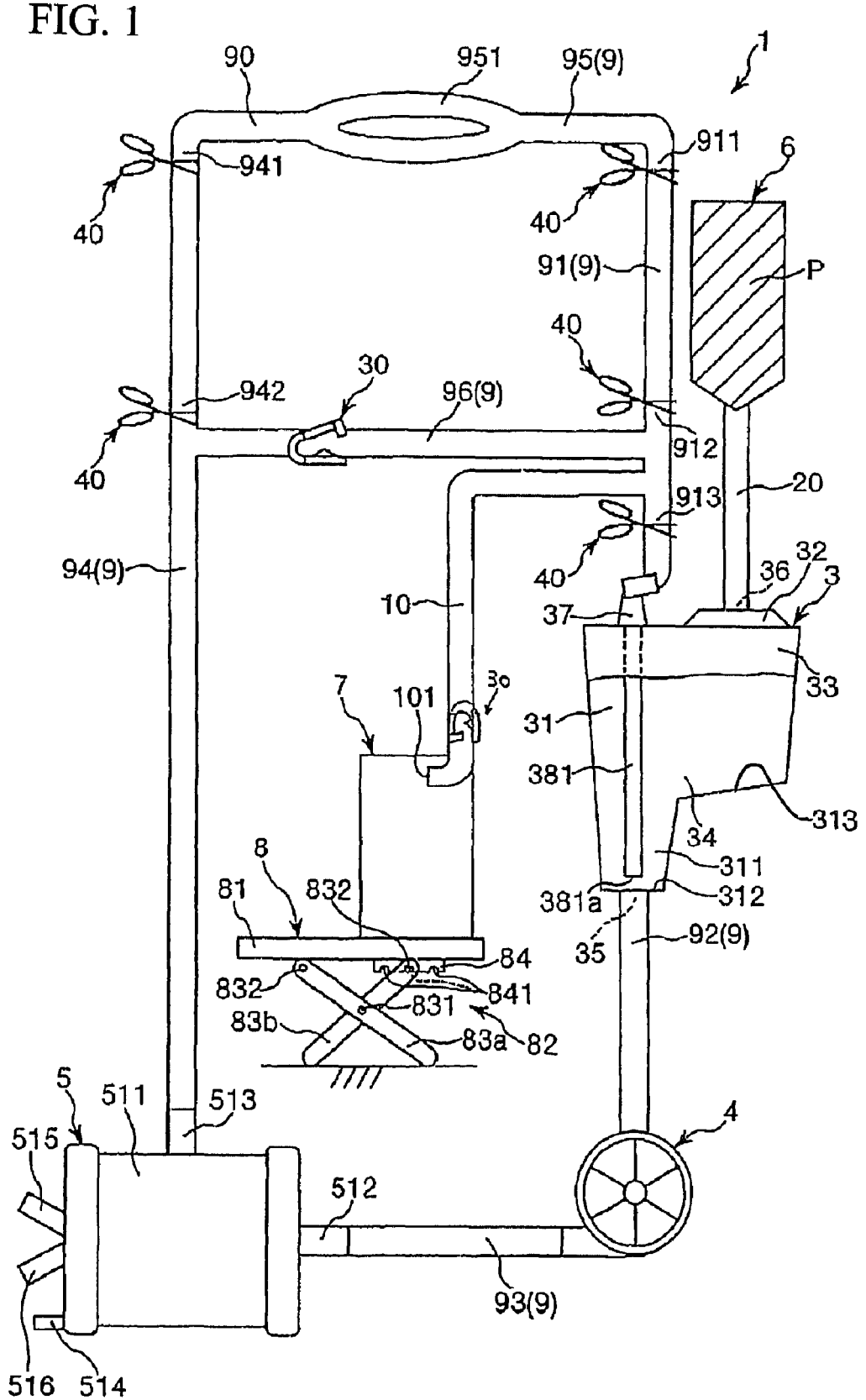
FIG. 1 is a schematic illustration of one embodiment of the circuitry of an extracorporeal circuit disclosed here, presenting one aspect of the sequential manner of use of the extracorporeal circuit.

Referring to FIGS. 1-11, an extracorporeal circuit 1 shown in FIG. 1 circulates blood B and is configured to perform retrograde autologous priming (RAP). RAP is a technique for hindering hemodilution by collecting a priming solution P as much as possible before normal extracorporeal circulation of blood B (which may be simply referred to as extracorporeal circulation) is performed (see FIG. 11) after the extracorporeal circuit 1 is primed (i.e., filled with the priming solution P).

As shown in FIG. 1, the extracorporeal circuit 1 includes a circuit body 9 composed of four transparent tubes (circuit tubes) 90, 92, 93, 96, a blood reservoir 3 connected to several of the tubes, a pump 4 for drawing blood, and an oxygenator 5. Moreover, the extracorporeal circuit 1 includes, in addition to these components, a feed bag 6 from which a priming solution P is fed, a transparent tube 20 linking the feed bag 6 and the blood reservoir 3, a transparent tube (branch line or branch tube) 10 that branches out from a tube 91 included in the circuit body 9, a collection bag 7 coupled to the tube 10, a collection bag supporting device 8 that supports the collection bag, and two clamps 30 to be used to open or close the tube 96 and the tube 10 respectively. The illustrated and described embodiment of the circuit shown in FIG. 1, prior to use, is a closed system.

In the present embodiment, for convenience' sake, the portion of the tube (first tube) 90 extending in an up-and-down direction on the blood reservoir 3 side (right side) of the tube 90 in FIG. 1 is referred to as the tube or tube segment 91. The portion of the tube 90 extending in the up-and-down direction on the oxygenator 5 side (left side) of the tube 90 in FIG. 1 is referred to as the tube or tube segment 94. The portion of the tube 90 extending in the right-and-left direction between the tube 91 and the tube 94 in FIG. 1 is referred to as the tube or tube segment 95. Thus, as will become more apparent from the description below, the tube 90 is comprised of a first tube segment 91 forming a venous line, a second tube segment 94 forming an arterial line, and a third tube segment 95 interconnecting or communicating with both the first and second tube segments 91, 94.

The blood reservoir 3 shown in FIG. 12 is used to temporarily store a liquid in the extracorporeal circuit 1 (for example, blood B drawn from the large vein or a priming solution P). The blood reservoir 3 includes a housing 33 composed of a housing body 31 and a cover 32. A liquid storage space 34 in which a liquid (blood) is received and temporarily stored is interiorly located within the housing 33.

The housing body 31 is shaped like a box having a projection 311 jutting or projecting downward in the left part of FIG. 12. Thus, the interior of the housing body 31 includes a larger upper portion (i.e., an upper portion of larger cross-sectional area) and the projection 311 defining a lower portion of smaller cross-sectional area. The housing body 31 thus includes a shelf 313 between the larger upper portion and the smaller lower portion. A tubular connecting port 35 communicating with the liquid storage space 34 is formed at the lower end of the projection 311.

The cover 32 is engaged with the upper end of the housing body 31 so that it covers the upper opening of the housing body 31. The tubular connecting ports 36, 37 are formed at predetermined positions in the cover 32.

The connecting ports 35-37 are coupled (connected) as mentioned below in the extracorporeal circuit 1. As shown in FIG. 11, the tube 91 that serves as a venous line during extracorporeal circulation is coupled to the connecting port 37. Namely, blood from a patient flows through the connecting port 37 and into the blood reservoir during extracorporeal circulation.

The tube 20 is coupled (connected) to the connecting port 36. The blood reservoir 3 and the feed bag 6 are linked by the tube 20, and the priming solution P is fed from the feed bag 6 to the blood reservoir 3.

The tube 92 is coupled (connected) to the connecting port 35. The blood reservoir 3 and the pump 4 are linked by the tube 92. When the pump 4 is started, liquid (blood B or priming solution P) is fed from the blood reservoir 3 to the oxygenator 5.

The blood reservoir 3 having the foregoing structure is used in a posture having the connecting ports 36, 37 located vertically upward and above the connecting port 35 which is located vertically downward or vertically lower than the connecting ports 36, 37.

Moreover, a tube (reservoir tube) 381 is coupled to the connecting port 37 and is positioned inside the housing 33. This allows the tube 381 to communicate with the tube 91 on the upper side thereof via the connecting port 37. Moreover, the lower end 381a of the tube 381 is open to the interior of the reservoir. As shown in FIG. 12, the lower end 381a of the tube 381 is located near the bottom 312 of the projection 311, and faces the bottom 312 or bottom surface of the downward projection 311. The lower end 381a of the tube 381 is vertically positioned between the bottom surface 312 of the downward projection 311 and the shelf 313, with the lower end 381a of the tube 381 being preferably vertically closer to the bottom surface 312 of the downward projection 311 than the shelf 313 of the housing body 31.

A filter member 382 shaped like a sac and sheathing or covering the tube 381 is disposed outside the tube 381. The upper end of the filter member 382 is supported by the cover 32.

The filter member 382 is configured to remove foreign matter or bubbles from blood. The material of the filter member 382 is a porous material that is fully permeable to blood.

Moreover, a filter member 392 also shaped like a sac is disposed on the housing 33 side of the connecting port 36. The upper end of the filter member 392 is supported by the cover 32.

The filter member 392 is configured to remove foreign matter or bubbles from the priming solution P, transfusional blood, or a replacement fluid. The material of the filter member 382 is a porous material that is fully permeable to the priming solution or blood.

Moreover, an antifoaming member (not shown) is interposed between the tube 381 and filter member 382 and disposed inside the filter member 392.

The material of the tube 381 is not limited to any specific material. For example, polycarbonate, polypropylene, polyvinyl chloride, or any other polymeric material will do.

Examples of the porous material to be used to fabricate the filter members 382, 392 include a mesh-type material, a woven fabric, or a nonwoven fabric. These materials may be used individually or may be combined.

Projecting out from the oxygenator 5 are several ports, including a blood inflow port 512 via which blood flows into the oxygenator 5, a blood outflow port 513 via which blood flows out of the oxygenator 5, a gas inflow port 514, a gas outflow port, a heat carrier inflow port 515, and a heat carrier outflow port 516. In addition, a hollow fiber membrane bundle in which numerous hollow fiber membranes having a gas exchange capability are integrated is stored in the oxygenator 5. Further, a filter member having the capability to trap bubbles may be stored to lie on the periphery of the hollow fiber membrane bundle.

The pump 4 transfers blood within the extracorporeal circuit 1 (circuit body 9). The pump 4, preferably in the form of a centrifugal pump, includes a rotator that rotates under the control of a control device to which the pump is operatively connected. The pump 4 can adjust the quantity of transferred blood according to the number of rotations of the rotator.

The pump 4 is interposed between the blood reservoir 3 and the oxygenator 5. The pump 4 is coupled o connected to both the tube 92, which is connected to the blood reservoir 3, and the tube 93, which is connected to the oxygenator 5 as shown in, for example, FIG. 1.

Figure 2:
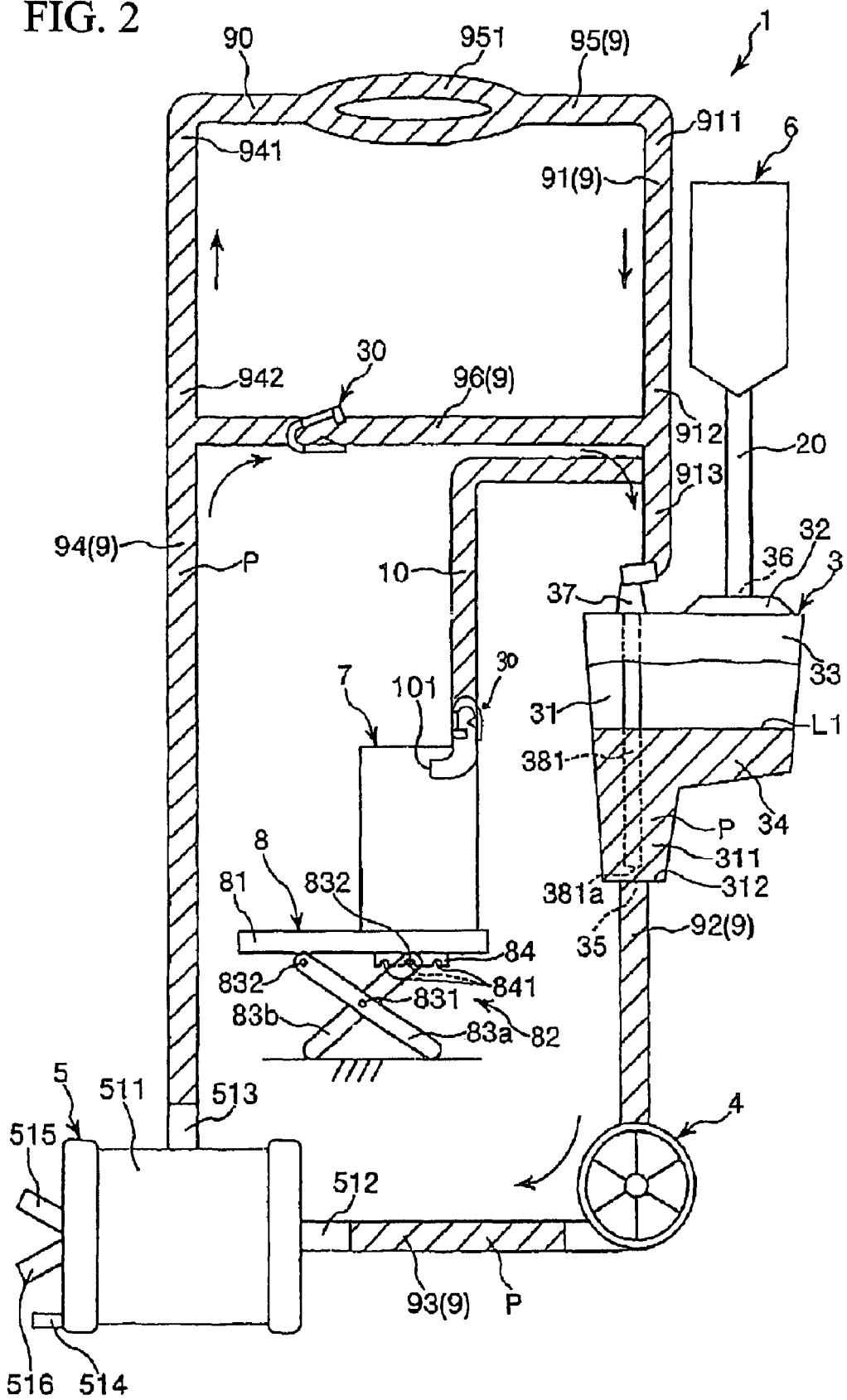
FIG. 2 is a schematic illustration of the circuitry of the extracorporeal circuit shown in FIG. 1, presenting another aspect of the sequential manner of use of the extracorporeal circuit.
Figure 3:
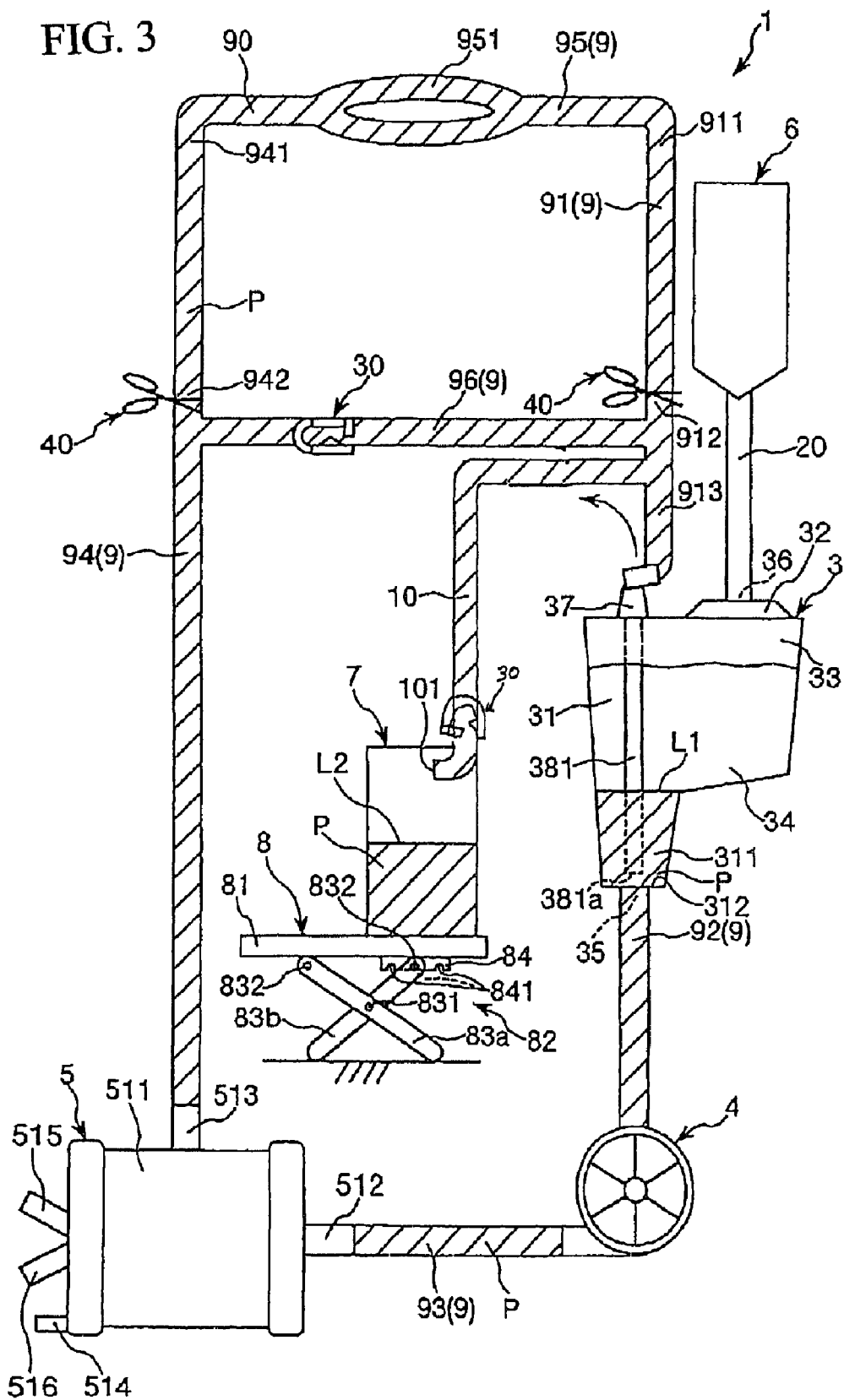
FIG. 3 is a schematic illustration of the circuitry of the extracorporeal circuit shown in FIG. 1, presenting another aspect of the sequential manner of use of the extracorporeal circuit.

As mentioned above, the circuit body 9 includes the tubes 90, 92, 93, 96. The tube 90 may be divided into three regions, namely tubes 91, 94, 95. As shown in FIGS. 1-3, the circuitry defining the extracorporeal circuit 1 includes the tube 91 serving as a venous line during extracorporeal circulation, the blood reservoir 3, the tube 92, the pump 4, the tube 93, the oxygenator 5, the tube 94 serving as an arterial line during extracorporeal circulation, and the tube 95 serving as a linkage line linking the ends of the tubes 91, 94. These parts of the circuit are arranged and connected in the order described.

Figure 5:
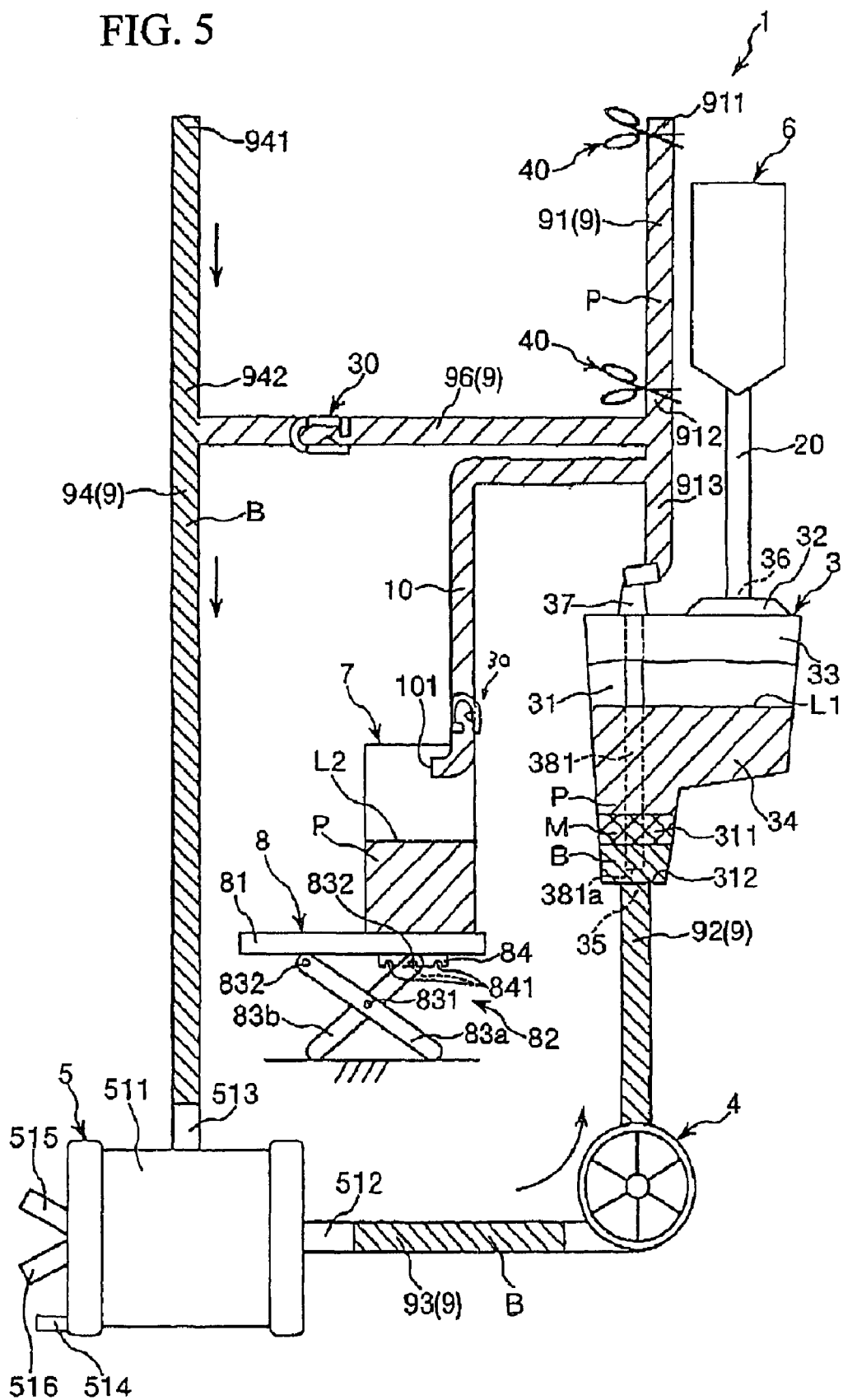
FIG. 5 is a schematic illustration of the circuitry of the extracorporeal circuit shown in FIG. 1, presenting another aspect of the sequential manner of use of the extracorporeal circuit.

The tube 95 is included in the extracorporeal circuit 1 until the extracorporeal circuit 1 is primed with the priming solution P (see, for example, FIG. 3). Thereafter, as shown in FIG. 5, as well as FIGS. 6-11, when blood B is extracorporeally circulated, the center part of the tube 95 that includes a loop 951 and the part of the tube 95 on the side of the tube 94 are cut out and removed, and the remaining parts of the tube 95 are coupled to indwelling venous-line and arterial-line catheters of a patient. In this state, the blood B is extracorporeally circulated.

Moreover, in the extracorporeal circuit 1, an intermediate portion (e.g., middle) of the tube 91 and an intermediate portion (e.g., middle) of the tube 94 are linked by the tube (second tube) 96. The tube 96 serves as a recirculation line when the extracorporeal circuit 1 is used to re-circulate blood B.

The tube 10 is coupled to the tube 91 at a region between the part to which the tube 96 is coupled to the tube 91 and the part to which the tube 96 is coupled to the blood reservoir 3. The tube 10 is coupled to the collection bag 7 which will be described in more detail later. The priming solution P is collected into the collection bag 7 by way of the tube 10.

The clamps 30 are attached to an intermediate portion of the tube 96 and an intermediate portion of the tube 10. The clamps 30 operate to press and close the tubes externally. Consequently, the tubes 10, 96 are brought to a closed state. When the pressing and closing by the clamps 30 is lifted or removed (i.e., when the clamps are opened), the tubes 96, 10 are brought to an open state.

The feed bag 6 is used to feed the priming solution P. The priming solution P is poured to such an extent that it can be fed to the entire extracorporeal circuit 1. Assuming that the lengths of the tubes 91, 94 which occupy a majority of the circuit body 9 range from, for example, 100 cm to 200 cm, the quantity of the poured priming solution P preferably ranges from 750 ml to 1500 ml.

The feed bag 6 is connected to the blood reservoir 3 at a position vertically above the tube 20. When the priming solution P flows into the liquid storage space 34 of the housing 33 of the blood reservoir 3, bubbles which may have flowed in together with the priming solution P are trapped by the filter member 392. Consequently, the bubbles can be inhibited or prevented from flowing out to the downstream side of the filter member 392.

Examples of suitable priming solution P include physiological saline or a lactated Ringer's solution.

The collection bag 7 is used to collect the priming solution P. The collection bag 7 is, similar to the feed bag 6, produced by fusing (heat fusion or high-frequency fusion) or bonding the perimeters of layered sheets, made of a soft resin such as polyvinyl chloride and flexible, in the form of a sac. The priming solution P is stored in spaces between the sheet layers. The volume of the collection bag 7 is nearly equal to or slightly larger than the volume of the feed bag 6.

The shape of the collection bag 7 is not limited to any specific shape. However, when the priming solution P is poured into the collection bag 7, that is, when the collection bag 7 is dilated, the collection bag should preferably be elongated.

The collection bag 7 may be placed so that the longitudinal direction of the bag is nearly parallel to a horizontal direction or will extend in a vertical direction. In the present embodiment, the collection bag 7 is placed so that the longitudinal direction thereof will extend nearly in the vertical direction.

Moreover, the open end 101 of the tube 10 (i.e., the liquid inflow port of the collection bag 7) should be located in the upper portion of the collection bag 7. The opening direction of the open end 101 should be a horizontal direction or a bit upward with respect to the horizontal direction. When the open end 101 of the tube 10 opens downward, if a liquid drips from the open end 101, air may enter the tube 10 by a volume equivalent to the quantity of the liquid. That is, if the open end 101 of the tube 10 is opened in the downward direction and a liquid drop falls from the open end 101 of the tube 10, an air drop generally equal in volume to the quantity or volume of the liquid drop may enter the tube, resulting in an air bubble in the tube. To avoid this potential problem, the opening direction in which the open end 101 of the tube 10 opens should preferably be restricted as mentioned above. As long as the opening direction is horizontal or upward, the open end 101 side of the tube 10 may invade into the collection bag 7 from the side wall of the collection bag or the top portion (upper wall) of the collection bag.

Moreover, when the collection bag 7 is used, the collection bag 7 is supported by (placed on) the collection bag supporting device 8. The collection bag supporting device 8 includes a placement unit 81 on which the collection bag 7 is placed, and a link mechanism 82 serving as a height adjusting means for adjusting the height of the placement unit 81.

In the illustrated embodiment, the placement unit 81 is in the form of a flat plate. The collection bag 7 is placed on the placement unit 81.

The link mechanism 82 includes two elongated members 83a, 83b supported to pivot on the center part 831. The upper end 832 of the elongated member 83a is supported so that it can pivot with respect to the placement unit 81, and the upper end 832 of the elongated member 83b is engaged with an engagement piece 84 disposed at a lower side of the placement unit 81. The engagement piece provides a mechanism permitting adjustment of the upper end 832 of the elongated member 83b relative to the placement unit 81. For example, three recesses (concave parts) 841 are formed in the engagement piece 84. By engaging the upper end 832 of the elongated member 83b in a selected one of the recesses 841, the height of the placement unit 81 can be appropriately set and adjusted.

By adjusting the height of the placement unit 81, the height of the liquid level L1 in the blood reservoir 3 can be adjusted. In other words, the height of the open end 101 of the tube 10 in the collection bag 7 can be set to a target height of the liquid level L1 (shown in FIG. 11) in the blood reservoir 3. Consequently, the priming solution P can be collected based on the principle of a siphon that will be described later.

Next, the operation of the extracorporeal circuit 1 will be described below.

[1] In an initial state shown in FIG. 1, the pump 4 is stopped. The clamp 30 attached to the tube 96 is left open, and the clamp 30 attached to the tube 10 is closed.

Three forceps 40 are attached to, or provided at spaced apart positions along, the tube 91 in the initial state. With respect to these three forceps 40, the positions (attached positions) of two of the forceps 40 along the tube are, in the circuitry shown in FIG. 1, between the joint where the tube 91 and the tube 95 join each other, and the joint where the tube 91 and tube 96 join each other. Stated differently, the two forceps 40 are positioned along the tube 91 at a position near the tube 95 (on the side of the tube 95) and at a position near the tube 96 (on the side of the tube 96) respectively. Moreover, the position (attached position) of the third forceps 40 is between the joint at which the tube 91 and the tube 96 join each other and the joint at which the tube 91 and the blood reservoir 3 (connecting port 37) join each other. Hereinafter, the parts of the tube 91 to which the three forceps 40 are attached are referred to as the forceps-attached part 911, the forceps-attached part 912, and the forceps-attached part 913 in that order from the tube 95 side thereof (the upper side in FIG. 1).

Two additional forceps 40 are attached to, or provided at spaced apart positions along, the tube 94 in the initial state. The attached positions of these two additional forceps 40 along the tube 94 are, in the circuitry shown in FIG. 1, between the joint where the tube 94 and the tube 95 join one another and the joint where the tube 94 and the tube 96 join each other. That is, the two additional forceps are positioned along the tube 94 at a position near the tube 95 (on the side of the tube 95) and at a position near the tube 96 (on the side of the tube 96) respectively. Hereinafter, the portions of the tube 94 to which the forceps 40 are attached are referred to as the forceps-attached part 941 and the forceps-attached part 942 in that order from the tube 95 side thereof (the upper side in FIG. 1).

The collection bag 7 is placed on the collection bag supporting device 8. The height at which the collection bag 7 is disposed is a height permitting the height of the open end 101 of the tube 10 in the collection bag 7 to square with (be even with or at the same height as) the target height of the liquid level L in the blood reservoir 3 (shown in FIG. 11). In the collection bag supporting device 8, the engagement of the elongated member 83b of the link mechanism 32 with the engagement piece 84 is adjusted so that the collection bag will be disposed at the desired height.

When the height of the collection bag 7 is designated as mentioned above, the priming solution P can be readily and quickly collected into the collection bag 7 according to the principle of a siphon to be described later.

[2] Thereafter, the tube 20 is coupled to the feed bag 6. Consequently, the priming solution P in the feed bag 6 flows into the blood reservoir 3 by way of the tube 20 due to a difference in height, and further flows in the direction of the arrow shown in FIG. 2. At this time, the pump 4 is started.

In other words, when the tube 20 is coupled to the feed bag 6, the priming solution P in the feed bag 6 sequentially passes through the tube 20 and the connecting port 36 of the blood reservoir 3 and is introduced into the housing 33. The priming solution P introduced into the housing 33 flows out through the connecting port 35. The priming solution P sequentially passes through the tube 92, pump 4, and the tube 93, and is fed to the oxygenator 5. The priming solution P further passes through the oxygenator 5 and flows into the tube 94. The priming solution P in the tube 94 is divided into two portions, one portion flowing into the tube 96 from an intermediate portion of the tube 94 and another portion continuing to flow in the tube 94 toward the end (downstream side) of the tube 94 in a direction towards the tube 95.

The priming solution P that flows into the tube 96 from the tube 94 sequentially passes through the tube 96 and the tube 91, and once again flows into the blood reservoir 3. In the tube 10, the air in the tube is displaced by the priming solution. The tube 10 is filled with the priming solution up to the position of the clamp 30. Moreover, the priming solution P that heads for or flows toward the tube 95 sequentially passes through the tube 95 and the tube 91, merges into the priming solution P, which has passed through the tube 96, in the intermediate portion of the tube 91, and once again flows into the blood reservoir 3. The liquid level L1 of the priming solution P in the blood reservoir 3 lies at a position higher than the position of the open end 101 of the tube 10.

Through the foregoing process, the entire extracorporeal circuit 1 is filled with the priming solution P, that is the entire extracorporeal circuit 1 is primed. Moreover, in the extracorporeal circuit 1, the liquid level L1 of the priming solution P in the blood reservoir 3 is set to a position above the lower end 381a of the tube 381 as seen in FIGS. 2-11. Consequently, when the priming solution P in the blood reservoir 3 is collected, the principle of a siphon can be utilized.

Moreover, as mentioned above, the tube 10 is occluded by the clamp 30. Therefore, the priming solution P in the extracorporeal circuit 1 can be reliably prevented from being unexpectedly collected into the collection bag 7.

In the state shown in FIG. 2, the priming solution P in the projection 311 of the blood reservoir 3, that is the quantity of priming solution equivalent to a depth from the liquid level L1 shown in FIG. 2 to the liquid level L1 shown in FIG. 3 represents an excess. At the next step [3], the excessive quantity is collected in the collection bag 7.

[3] As shown in FIG. 3, the clamp 30 attached to the tube 96 is closed. The forceps 40 are attached to the forceps-attached part 912 of the tube 91, and the forceps 40 are attached to the forceps-attached part 942 of the tube 94. At this time, the pump 4 is stopped.

Thereafter, the clamp 30 attached to the tube 10 is opened. This causes the tube 91 and collection bag 7 to communicate with each other by way of the tube 10. The priming solution P is transferred and collected in the collection bag 7 as described below due to a difference in height of the liquid level L1 in the blood reservoir 3 from the liquid inflow port of the collection bag 7 (the open end 101 of the tube 10), that is due to the principle of a siphon. The open end 101 of the tube 10 through which liquid flows into the collection bag 7 is located at the target height of the liquid level L1.

When the clamp 30 of the tube 10 is opened, the priming solution P in the tube 10 flows into the collection bag 7. When the priming solution P begins flowing into the collection bag 7, the priming solution P in the blood reservoir 3 passes through the tube 381 accordingly, and is then introduced (thrust) into the tube 91. The priming solution P introduced into the tube 91 flows into the collection bag 7 by way of the tube 10. This phenomenon persists until the liquid level L1 in the blood reservoir 3 reaches (is lowered to) the same height as the height of the open end 101 of the tube 10 in the collection bag 7 (the principle of a siphon). Consequently, the excessive quantity of priming solution P in the blood reservoir 3 can be readily and quickly collected.

As mentioned above, in the extracorporeal circuit 1, once the height of the open end 101 of the tube 10 in the collection bag 7 is appropriately adjusted, a quantity of the priming solution P determined by this height flows into the collection bag 7. Consequently, when the extracorporeal circuit 1 is manipulated, an operator need not be conscious of whether the position of the liquid level L1 in the blood reservoir 3 is lowered below a predetermined position.

Figure 4:
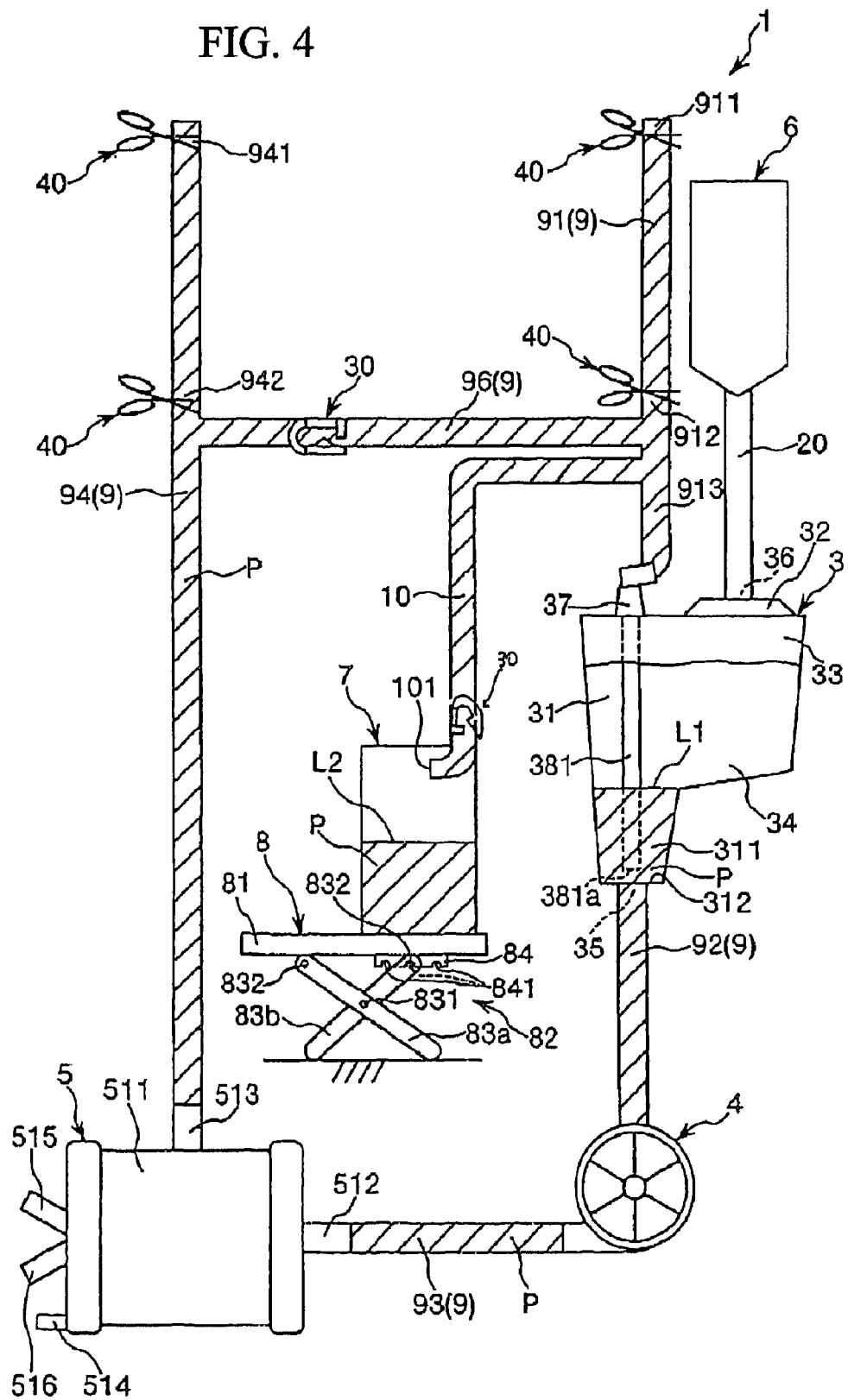
FIG. 4 is a schematic illustration of the circuitry of the extracorporeal circuit shown in FIG. 1, presenting another aspect of the sequential manner of use of the extracorporeal circuit.

[4] After the priming solution P is collected, the clamp 30 attached to the tube 10 is reclosed as shown in FIG. 4, meaning that the clamp 30 is once again closed. Also, the forceps 40 are attached to the forceps-attached part 911 of the tube 91, and the forceps 40 are attached to the forceps-attached part 941 of the tube 94.

In this state, the tube 95 is cut as mentioned above, and coupled to an arterial-line catheter that is one of the two indwelling catheters of a patient.

[5] In the state shown in FIG. 4, two forceps 40 are detached from the tube 94. At this time, blood B flows from the patient to the tube 94 in the direction of the arrow in FIG. 5 due to blood pressure. The flow of the blood B is opposite to that in normal extracorporeal circulation.

The blood B flowing into the tube 94 sequentially passes through the oxygenator 4, tube 93, pump 4, and tube 92, and flows into the projection 311 of the housing 33 through the connecting port 35 of the blood reservoir 3. Due to the blood B, the priming solution P in the tube 94, oxygenator 4, tube 93, pump 4, and tube 92 is thrust into the housing 33. In other words, the priming solution P in the tube 94, oxygenator 4, tube 93, pump 4, and tube 92 is displaced by the blood B.

Moreover, when the blood B flows into the projection 311, the blood B is mixed with the priming solution P in the projection 311. Namely, part of the priming solution P in the projection 311 is colored in red that is lighter than the color of the blood B. In FIG. 5, a mixture M having the priming solution P and blood B mixed together is shown positioned between the vertically higher priming solution P and the vertically lower blood B in the projection 311.

Figure 6:
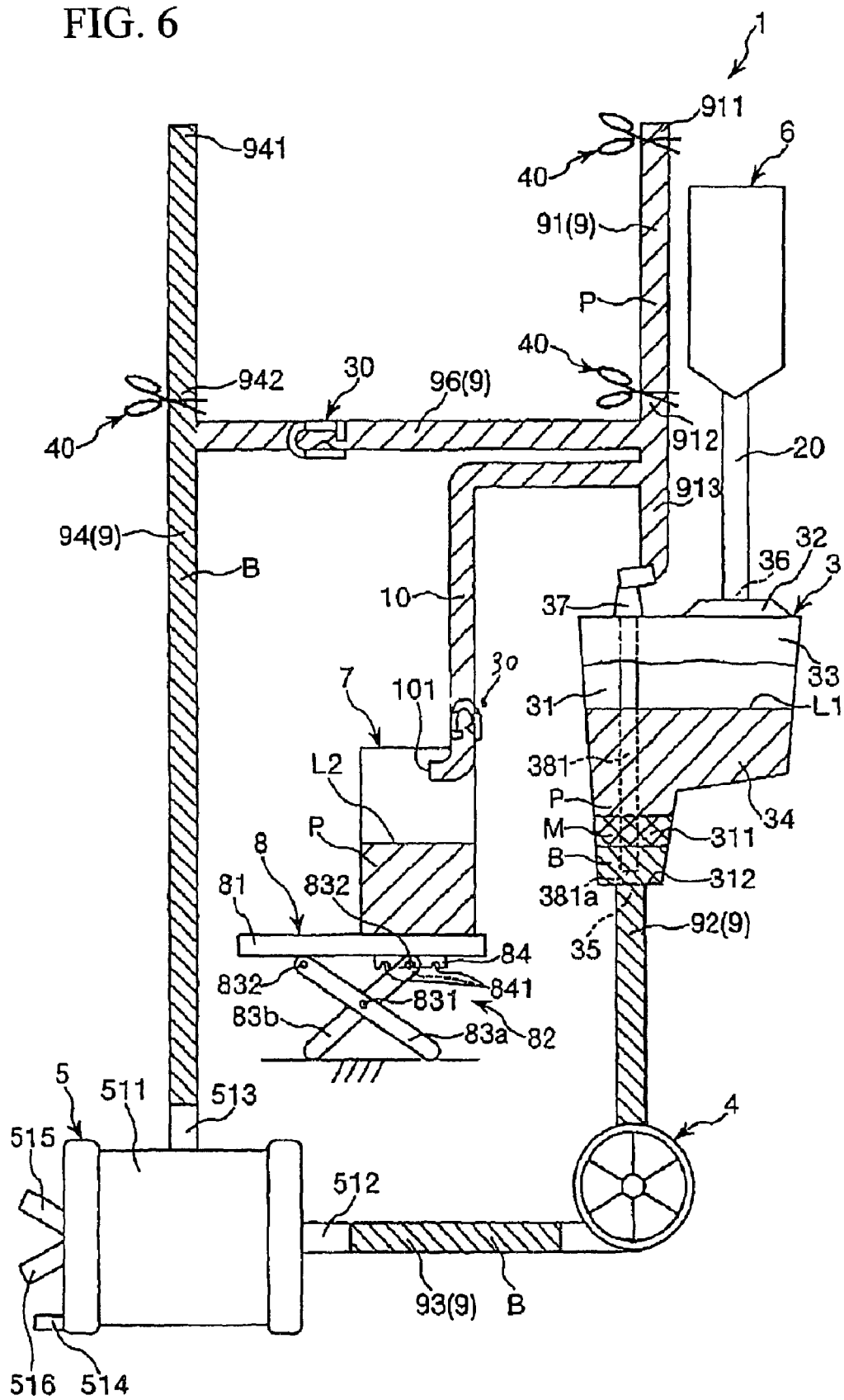
FIG. 6 is a schematic illustration of the circuitry of the extracorporeal circuit shown in FIG. 1, presenting another aspect of the sequential manner of use of the extracorporeal circuit.

[6] After the coloring is recognized, the forceps 40 are once again attached to the forceps-attached part 942 of the tube 94 as shown in FIG. 6. Consequently, the flow of the blood B into the tube 94 ceases. Accordingly, the rise of the liquid level L1 in the blood reservoir 3 stops.

In the state shown in FIG. 6, the priming solution P in the tube 94, the oxygenator 5, the tube 93, the pump 4, and the tube 92 is reserved in the blood reservoir 3. Further, the priming solution P is left intact in a range from the tube 381 in the blood reservoir 3 to the part of the tube 91 to which the tube 10 is coupled. At the next step [7], the priming solution is collected in the collection bag 7.

Figure 7:
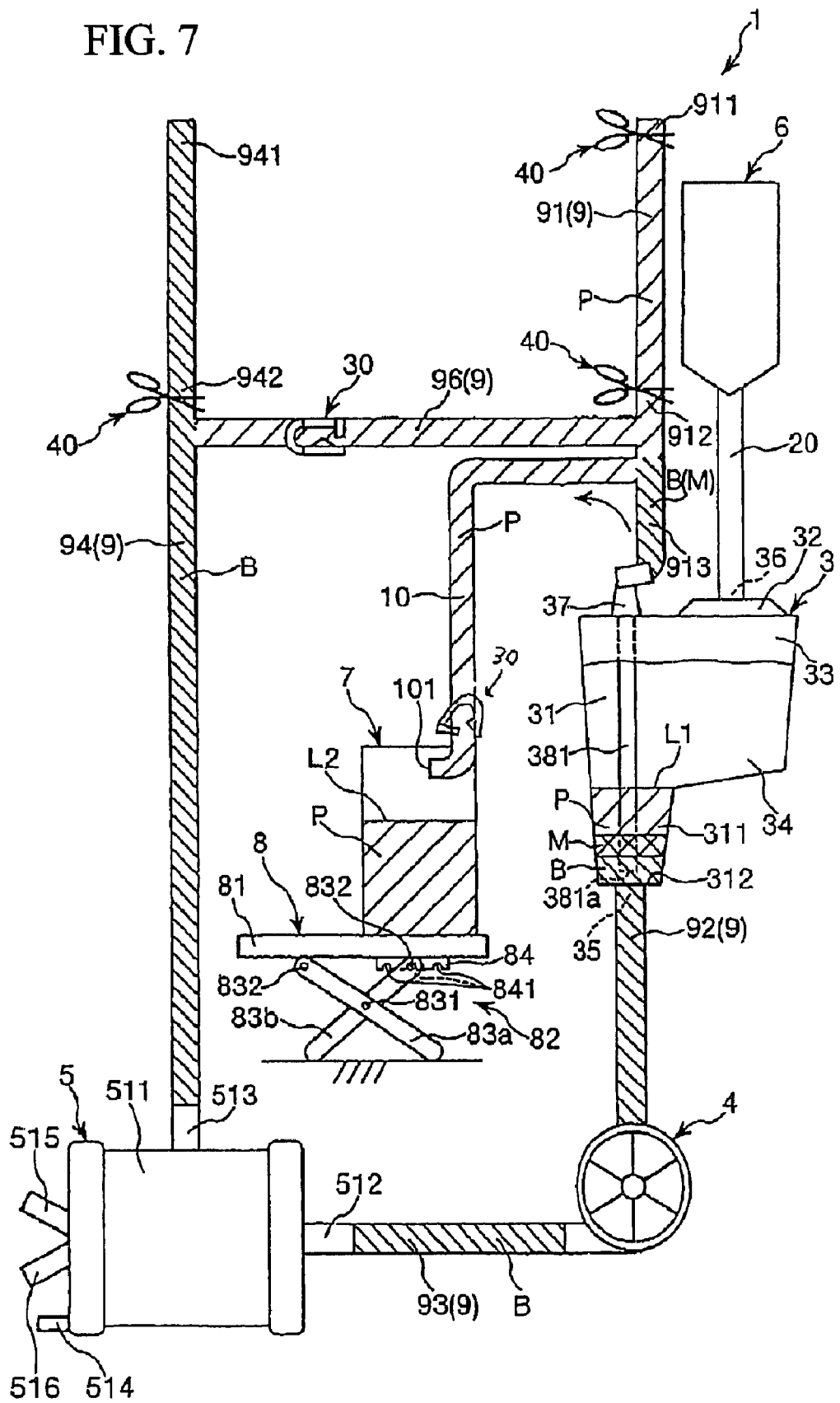
FIG. 7 is a schematic illustration of the circuitry of the extracorporeal circuit shown in FIG. 1, presenting another aspect of the sequential manner of use of the extracorporeal circuit.

[7] The clamp 30 attached to the tube 10 as shown in FIG. 6 is reopened as illustrated in FIG. 7. Consequently, the priming solution P (including the mixture M) in the blood reservoir 3, and the priming solution P in the range from the tube 381 in the blood reservoir 3 to the part of the tube 91 to which the tube 10 is coupled flow into the collection bag 7 by way of the tube 10 based on the principle of a siphon similar to the process [3] described above. The inflow of the priming solution P continues until the liquid level L1 in the blood reservoir 3 comes to the same height as the height of the open end 101 of the tube 10 in the collection bag 7.

As mentioned above, at the step [7], the priming solution P can be readily and quickly collected by performing the simple manipulation of opening the clamp 30.

Figure 8:
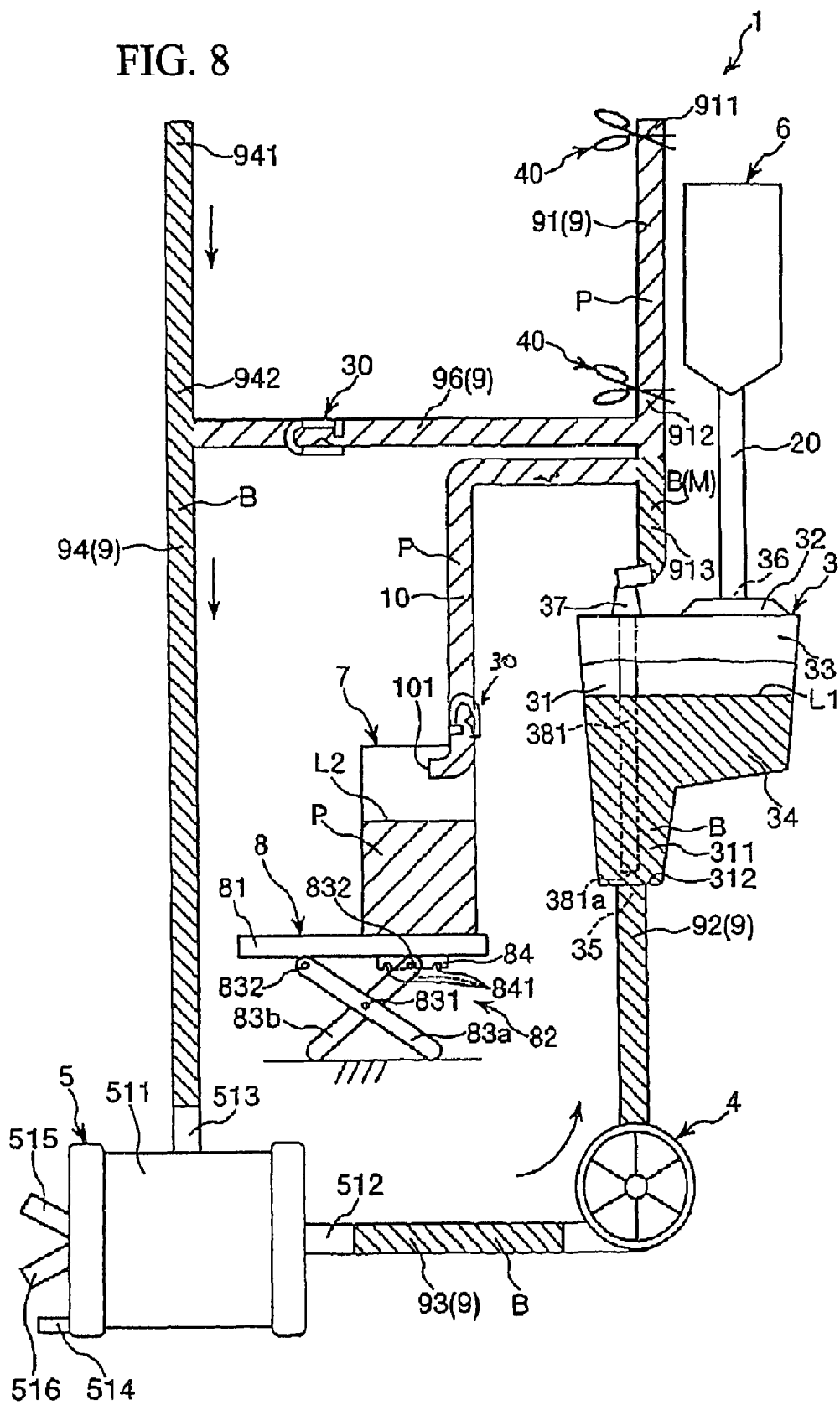
FIG. 8 is a schematic illustration of the circuitry of the extracorporeal circuit shown in FIG. 1, presenting another aspect of the sequential manner of use of the extracorporeal circuit.

[8] After the inflow of the priming solution P ceases, the clamp 30 attached to the tube 10 is closed again as shown in FIG. 8. Thereafter, the forceps 40 are detached from the forceps-attached part 942 of the tube 94.

In this state, blood B flows from the patient in the direction of the arrow in FIG. 8 due to blood pressure. Consequently, in the extracorporeal circuit 1, the tube 94, the oxygenator 5, the tube 93, the pump 4, the tube 92, and the blood reservoir 3 are filled with the blood B as depicted in FIG. 8.

[9] After a predetermined quantity of the blood B is poured into or enters the blood reservoir 3, the forceps 40 are reattached to the forceps-attached part 942 of the tube 94. Consequently, the inflow of the blood B to the tube 94 ceases. Moreover, the forceps 40 are attached to the forceps-attached part 913 of the tube 91. Thereafter, the tube 91 is coupled to the indwelling venous-line catheter of the patient.

Figure 9:
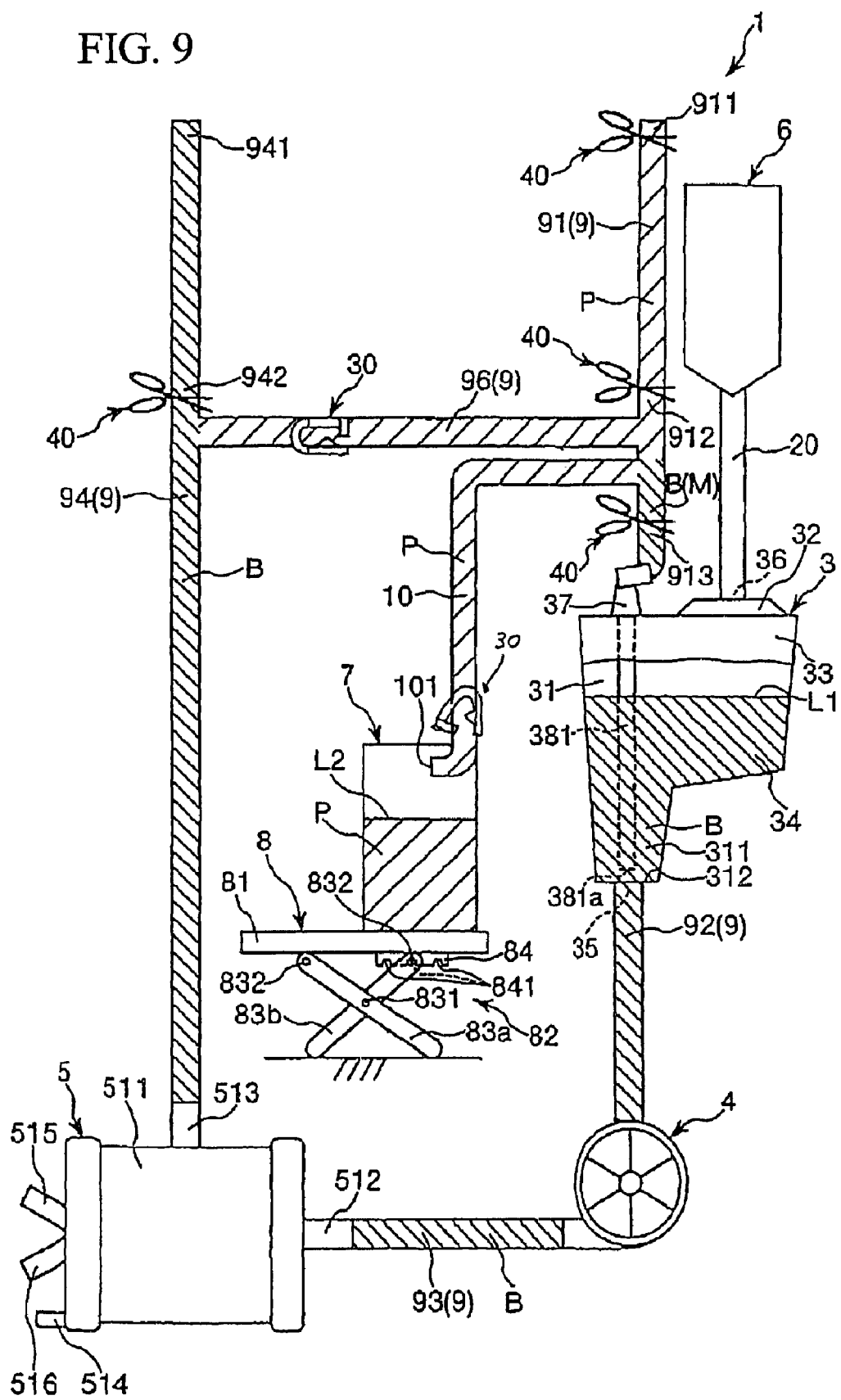
FIG. 9 is a schematic illustration of the circuitry of the extracorporeal circuit shown in FIG. 1, presenting another aspect of the sequential manner of use of the extracorporeal circuit.
Figure 10:
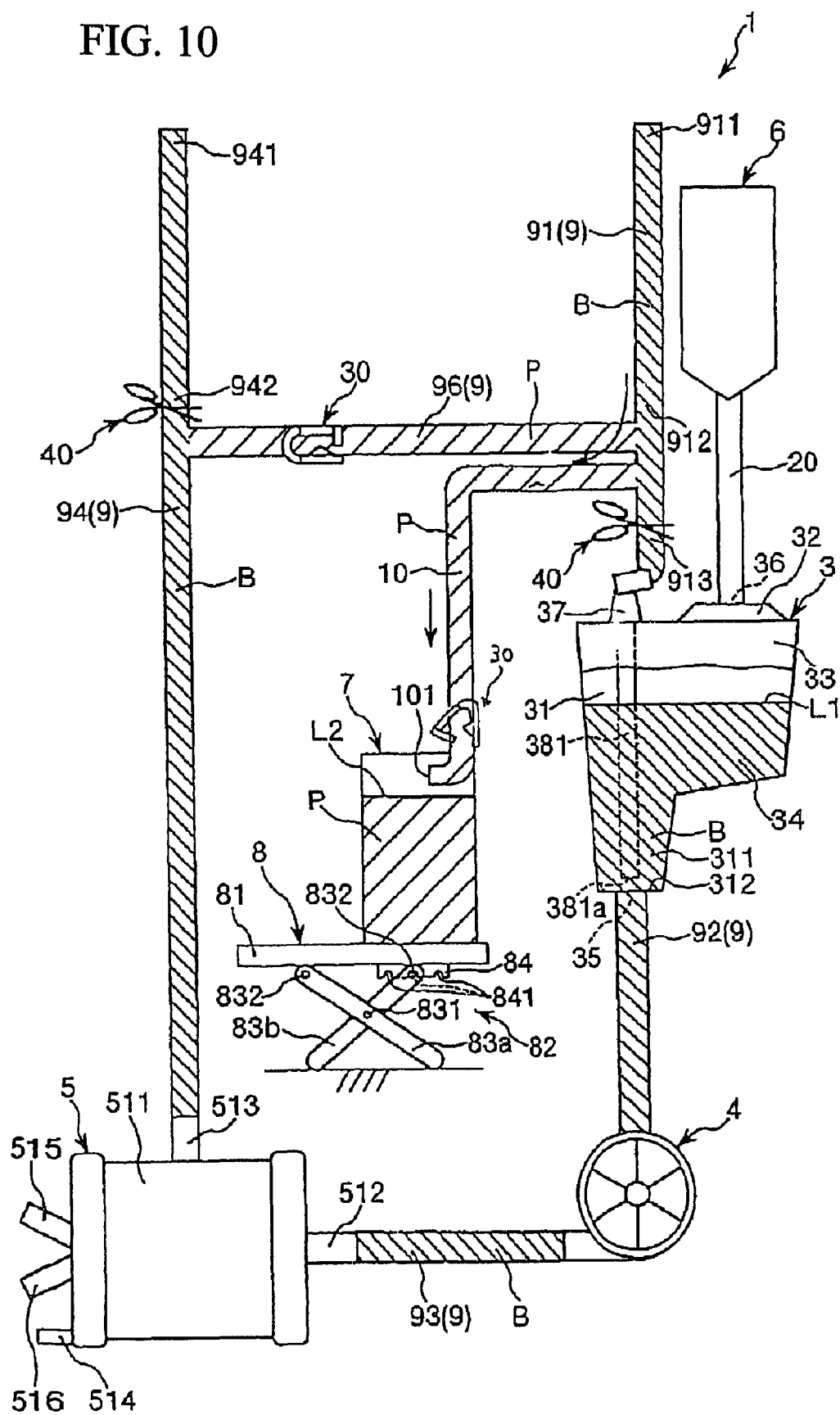
FIG. 10 is a schematic illustration of the circuitry of the extracorporeal circuit shown in FIG. 1, presenting another aspect of the sequential manner of use of the extracorporeal circuit.

In this state, the clamp 30 attached to the tube 10 is reopened as shown in FIG. 9.

[10] In the state shown in FIG. 9, the forceps 40 are detached from the forceps-attached parts 911, 912 of the tube 91. At this time, the blood B flows from the patient into the tube 91 due to a blood pressure. The blood B having flowed into the tube 91 thrusts the priming solution P in the tube 91 in the direction of the arrow in FIG. 10. Consequently, the priming solution P in the tube 91 is collected in the collection bag 7 by way of the tube 10.

[11] After the priming solution P in the tube 91 is displaced by the blood B, the clamp 30 attached to the tube 10 is re-closed. Thereafter, both the forceps 40 attached to the forceps-attached part 913 of the tube 91 and the forceps 40 attached to the forceps-attached part 942 of the tube 94 are detached.

In this state, the blood B flows in the direction of the arrow in FIG. 11 due to a difference in height and a patient's blood pressure. Moreover, at this time, the pump 4 is restarted.

Specifically, when the pump 4 is started, the blood B drawn from the patient passes through the tube 91 (venous line), and flows into the blood reservoir 3. In the blood reservoir 3, bubbles are removed from the blood B owing to the operation of the filter member 382. The blood B having bubbles removed therefrom flows out of the connecting port 35 of the blood reservoir 3, passes through the pump 4, and is fed to the oxygenator 5. In the oxygenator 5, the blood B is subjected to gas exchange (oxygenated and decarboxylated). The blood B having been subjected to gas exchange passes through the tube 94 (arterial line) and returns to the patient.

Owing to the above operation, after the extracorporeal circuit 1 is primed, when the priming solution P is displaced by the blood B, the priming solution P can be readily and quickly collected by performing the relatively simple operation of manipulating the clamp 30 attached to the tube 10. Consequently, the procedure can quickly proceed to the extracorporeal circulation step (step [11]) at which the extracorporeal circuit 1 is employed or put into operation.

Moreover, the extracorporeal circuit 1 can thrust the priming solution P into the collection bag 7 using the blood B, that is the system can perform RAP. The blood B in the extracorporeal circuit 1 can be prevented from being diluted with the priming solution P.

Moreover, in the extracorporeal circuit 1, in the state shown in FIG. 11, after the forceps 40 are attached to the forceps-attached part 912 of the tube 91 and the forceps-attached part 942 of the tube 94 respectively, the clamp 30 of the tube 96 can be opened. In this case, the blood B coming out of the oxygenator 5 sequentially passes through the tube 96 (recirculation line) and blood reservoir 3, and then returns to the pump 4. The blood B is therefore repeatedly circulated (recirculated) over an annular path including the pump 4 and oxygenator 5.

Figure 13:
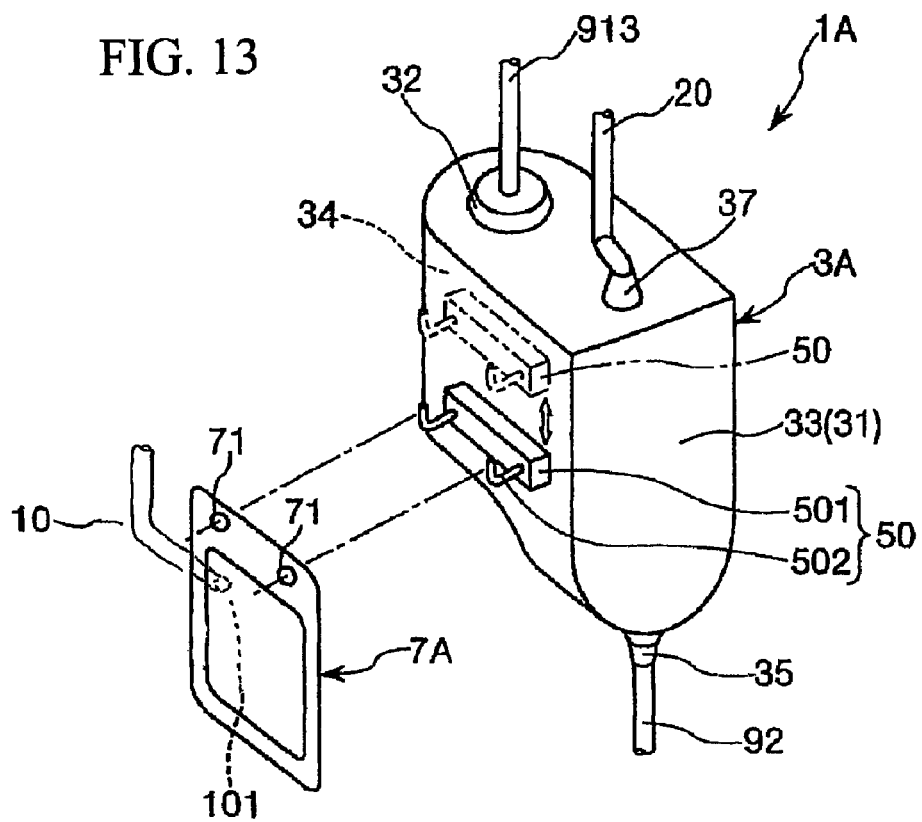
FIG. 13 is a perspective view of a blood reservoir and a collection bag included in an extracorporeal circuit according to a second embodiment.

FIG. 13 is a perspective view of a blood reservoir and a collection bag included in an extracorporeal circuit according to a second embodiment.

The second embodiment will be described below, primarily with reference to features in this embodiment that differ from the features in the first embodiment. Features in this second embodiment that are similar to those in the first embodiment are designated by common reference numerals and a detailed description of such features will not be repeated here.

The second embodiment is identical to the first embodiment except that the structures of the blood reservoir and the collection bag are different.

A collection bag 7A of an extracorporeal circuit 1A shown in FIG. 13 is produced by fusing (or bonding) the perimeters of layered sheets, which are flexible and made of a soft resin such as polyvinyl chloride, in the form of a sac, and then forming two holes 71 in the fused perimeters. The holes 71 are formed in spaced apart relation to one another and are located in the upper part of the collection bag 7A in a use state of the collection bag 7A.

A holding member 50 that holds the collection bag 7A (on which the collection bag is hung) is disposed on the flank of the blood reservoir 3A (the housing 33). The holding member 50 includes a plate-shaped support element 501 and two hooks 502 borne on and extending outwardly away from the face of the support plate 501.

The support element 501 is made of the same material as, for example, that of the housing body 31 of the blood reservoir 3A. A double-sided adhesive tape is bonded to the back of the support plate 501. Owing to the presence of the double-sided adhesive tape, the holding member 50 can be attached to or detached from the blood reservoir 3A. The height at which the holding member 50 is disposed on the blood reservoir 3A can be changed (as indicated by the two positions shown in FIG. 13—the solid line position and the position represented by alternating long and two short dash lines).

The hooks 502 are L-shaped and made of a metallic material, for example stainless steel. The hooks 502 are inserted into the respective holes 71 in the collection bag 7A, whereby the collection bag 7A is hung on the support element (the hooks 502 of the supporting element) while being used.

The adhesive strength of the double-sided adhesive tape is set to such a level that when the collection bag 7A is hung on the holding member 50, even if the priming solution P is poured into the collection bag 7A, the holding member 50 will not come off the blood reservoir 3A.

As mentioned above, in the extracorporeal circuit 1A, the holding member 50 is designed so that the disposed height of the collection bag 7A on the blood reservoir 3A can be adjusted. Consequently, a quantity of the priming solution P collected into the collection bag 7A can be appropriately designated according to the situation.

Figure 14:
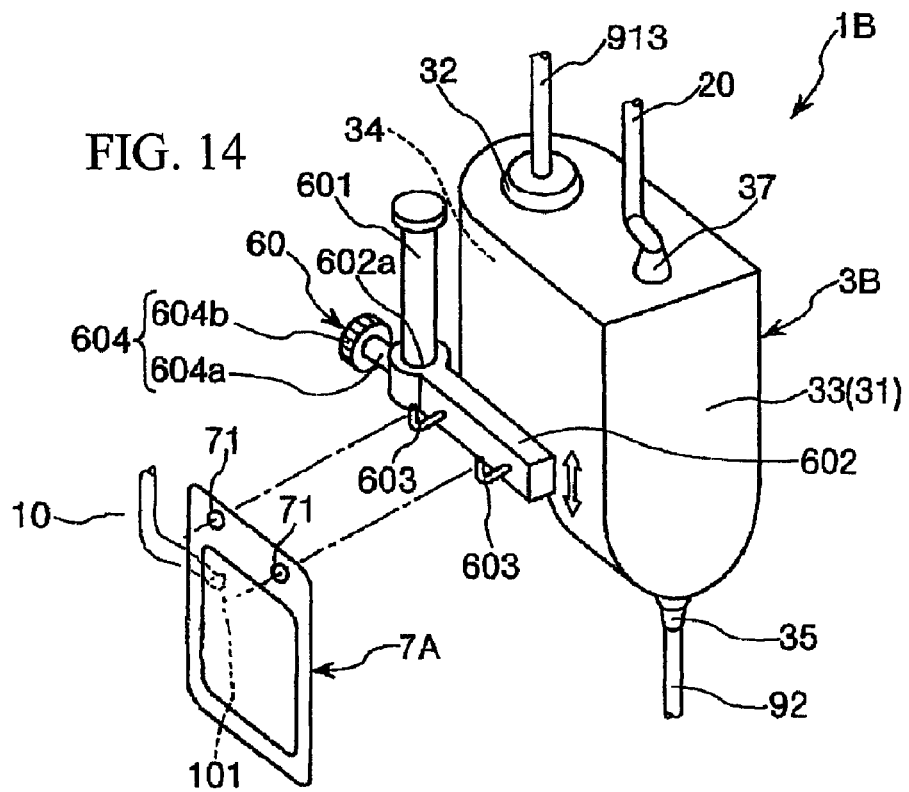
FIG. 14 is a perspective view of a blood reservoir and a collection bag included in an extracorporeal circuit according to a third embodiment.

FIG. 14 is a perspective view of a blood reservoir and a collection bag included in an extracorporeal circuit according to a third embodiment.

The third embodiment will be described below, primarily with reference to features in this embodiment that differ from the features in the second embodiment. Features in this third embodiment that are similar to those in the second embodiment are designated by common reference numerals and a detailed description of such features will not be repeated here.

This embodiment is identical to the second embodiment except for differences in the structure of the blood reservoir.

A holding mechanism 60 that holds the collection bag 7A (on which the collection bag 7A is hung) is disposed on the flank of a blood reservoir 3B (housing 33) included in an extracorporeal circuit 1B shown in FIG. 14. The holding mechanism 60 includes a column 601 having the lower end thereof borne by the blood reservoir 3B, a moving member 602 that is movable in the longitudinal direction of the column 601, two hooks 603 borne by and extending outwardly away from the moving member 602, and a setscrew (locking member) 604 that locks the moving member 602 to the column 601. The column 601 has a cylindrical shape.

The moving member 602 is formed as an elongated member. One of the elongated member forming the moving member 602 has a hole 602a through which the column 601 penetrates. A female screw that reaches (i.e., communicates with) the hole 602a is threaded in the flank of the moving member 602.

The hooks 603 are L-shaped, and made of a metallic material, for example stainless steel. Moreover, the hooks 603 are disposed is spaced apart relation to one another in the longitudinal direction of the moving member 602. When the hooks 603 are inserted into the holes 701 in the collection bag 7A, the collection bag 7A can be used while being hung on the blood reservoir (or abutting against the blood reservoir).

The setscrew 604 includes a male screw portion 604a, and a head portion 604b attached to one end of the male screw portion 604a. The setscrew 604 has the male screw portion 604 thereof meshed with the female screw threaded in the moving member 602, and has the other end of the male screw portion 604 thereof engaged with the periphery of the column 601. Consequently, the moving member 602 can be locked to the column 601 (i.e., the vertical position of the moving member 602 can be fixed relative to the column 601). Thus, the collection bag 7A can be held at a predetermined position (height).

Moreover, when the setscrew 604 is loosened, the moving member 602 is unlocked and can be moved. Consequently, the disposed height of the collection bag 7A on the blood reservoir 3B can be changed.

As mentioned above, in the extracorporeal circuit 1B, the holding mechanism 60 is designed so that the disposed height of the collection bag 7A on the blood reservoir 3A can be adjusted by moving the moving member 602. Consequently, the quantity of priming solution P to be collected into the collection bag 7A can be appropriately designated according to the situation.

Moreover, since the column 601 has a cylindrical shape, the moving member 602 unlocked from the setscrew 604 can be turned on (i.e., can rotate relative to) the axis of the column 601. Consequently, the orientation of the held collection bag 7A can be varied depending on, for example, the standing position of a user. Eventually, the state of the priming solution P being collected into the collection bag 7A can be readily discerned (checked).

The invention here is not limited to the embodiments of the extracorporeal circuit which are shown in the drawings and described above. The components of the extracorporeal circuit may be replaced with alternative features which exhibit the same or similar functions. In addition, components or features beyond those shown and described here can be provided.

The extracorporeal circuit may be a combination of two or more of the aforesaid embodiments (constituent features).

Also, the feed bag and collection bag are not limited to those made of a soft resin material but may be bags made of a hard resin material such as polypropylene. Additionally, in the embodiments, clamps are used to open or close tubes. However, other features such as valves can be utilized instead.

The extracorporeal circuit disclosed here makes it possible to relatively quickly collect a priming solution when the priming solution is displaced by blood after the priming solution is fed to the extracorporeal circuit in order to prime the extracorporeal circuit. After the extracorporeal circuit is primed, when a priming solution is displaced by blood, that is retrograde autologous priming (RAP) is performed, the priming solution can be readily and quickly collected by performing simple manipulations on the extracorporeal circuit. Consequently, when the extracorporeal circuit is used to perform extracorporeal circulation, a procedure can quickly proceed to the next step (extracorporeal circulation step). Also, in the extracorporeal circuit, since the priming solution is collected, hemodilution caused by the priming solution can be inhibited or prevented.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An extracorporeal circuit for extracorporeally circulating blood, comprising:
    a circuit body for circulating liquid through a plurality of extracorporeal circuit components, the circuit body comprising a plurality of tube segments;
    a blood reservoir comprising one of the extracorporeal circuit components, the blood reservoir possessing an interiorly located storage chamber in which a liquid is received, the storage chamber having a bottom surface;
    a tube communicating with a first one of the tube segments, the tube possessing a lower end positioned in the storage space of the blood reservoir adjacent the bottom surface of the storage chamber;
    a branch line branching out from an intermediate portion of the first tube segment;
    a collection container communicating with the branch line and into which liquid in the storage chamber flows by way of the branch line; and
    height adjusting means for adjusting a height of the collection container.

2. The extracorporeal circuit according to claim 1, wherein the reservoir includes first and second connecting ports, the first tube segment being a venous line connected to the first connecting port to communicate the venous line with the tube, the second connecting port being connectable to a source of priming solution.

3. The extracorporeal circuit according to claim 1, wherein the reservoir includes first and second connecting ports, the first tube segment being a venous line connected to the first connecting port to communicate the venous line with the tube, and further comprising a feed bag containing priming solution, the feed bag being connected to the second connecting port.

4. The extracorporeal circuit according to claim 1, wherein the tube is a reservoir tube, the circuit body comprising at least first and second tubes, the first tube segment being a part of the first tube and forming a venous line, the plurality of tube segments comprising second and third tube segments that are a part of the first tube, the second tube segment forming an arterial line, the third tube segment extending between and communicating with the first and second tube segments, and the second tube extending between and communicating with the first and second tube segments.

5. The extracorporeal circuit according to claim 4, wherein the second tube is connected to the first tube segment at a first connection point, the first tube segment being connected to a connecting port of the blood reservoir at a second connection point, the branch line being connected to the first tube segment at a position between the first and second connection points.

6. An extracorporeal circuit for extracorporeally circulating blood, comprising:
- a circuit body for circulating liquid through a plurality of extracorporeal circuit components, the circuit body comprising a plurality of tube segments;
- a blood reservoir comprising one of the extracorporeal circuit components, the blood reservoir possessing an interiorly located storage chamber in which a liquid is received, the storage chamber having a bottom surface;
- a tube communicating with a first one of the tube segments, the tube possessing a lower end positioned in the storage space of the blood reservoir adjacent the bottom surface of the storage chamber;
- a branch line branching out from an intermediate portion of the first tube segment;
- a collection container communicating with the branch line and into which liquid in the storage chamber flows by way of the branch line; and
- wherein the branch line extends into the collection container, and the open end of the branch line opens in a horizontal direction in the collection container or in a direction upward with respect to the horizontal direction in the collection container when the collection container is positioned upright in use.

7. An extracorporeal circuit for extracorporeally circulating blood, comprising:
- a circuit body comprised of a plurality of circuit tubes including a first circuit tube, the first circuit tube being comprised of a plurality of tube segments including a first tube segment constituting a venous line adapted to be connected to a vein of a patient during extracorporeal circulation and a second tube segment constituting an arterial line adapted to be connected to an artery of the patient during extracorporeal circulation;
- a blood reservoir connected to the first tube segment, the blood reservoir including an interiorly located storage chamber for temporarily storing liquid,
- a pump positioned along the circuit body to convey liquid in the circuit body, the pump being connected to the reservoir;
- an oxygenator connected to the second tube segment and configured to perform gas exchange on blood flowing through the circuit body;
- a priming solution feeding unit containing priming solution, the priming solution feeding unit being in communication with the blood reservoir;
- a reservoir tube having one end communicating with the first tube segment constituting the venous line and an opposite end which is open and which is positioned adjacent a bottom of the storage chamber;
- a branch line branching communicating with and branching out from an intermediate portion of the first tube segment constituting the venous line;
- a collection container communicating with the branch line and into which the priming solution in the storage chamber is collected by way of the branch line;
- after the priming solution is fed from the priming solution feeding unit to the storage chamber to prime at least the storage chamber, the priming solution in the storage chamber is displaced by blood and is transferred to the collection container due to a difference in height of liquid in the storage chamber relative to liquid in the collection container; and
- wherein the branch line extends into the collection container, and the open end of the branch line opens in a horizontal direction in the collection container or in a direction upward with respect to the horizontal direction in the collection container when the collection container is positioned upright in use.

8. The extracorporeal circuit according to claim 7, wherein the blood reservoir includes first and second connecting ports, the first tube segment constituting the venous line being connected to the first connecting port to communicate the venous line with the reservoir tube, the second connecting port being connected to the priming solution feeding unit.

9. The extracorporeal circuit according to claim 7, wherein the first circuit tube also comprises a third tube segment extending between and communicating with the first and second tube segments, the circuit body also comprising a second tube extending between and communicating with the first and second tube segments.

10. The extracorporeal circuit according to claim 9, wherein the second tube is connected to the first tube segment at a first connection point, the first tube segment being connected to a connecting port of the blood reservoir at a second connection point, the branch line being connected to the first tube segment at a position between the first and second connection points.

11. An extracorporeal circuit for extracorporeally circulating blood, comprising:
- a circuit body comprised of a plurality of circuit tubes including a first circuit tube, the first circuit tube being comprised of a plurality of tube segments including a first tube segment constituting a venous line adapted to be connected to a vein of a patient during extracorporeal circulation and a second tube segment constituting an arterial line adapted to be connected to an artery of the patient during extracorporeal circulation;
- a blood reservoir connected to the first tube segment, the blood reservoir including an interiorly located storage chamber for temporarily storing liquid,
- a pump positioned along the circuit body to convey liquid in the circuit body, the pump being connected to the reservoir;
- an oxygenator connected to the second tube segment and configured to perform gas exchange on blood flowing through the circuit body;
- a priming solution feeding unit containing priming solution, the priming solution feeding unit being in communication with the blood reservoir;
- a reservoir tube having one end communicating with the first tube segment constituting the venous line and an opposite end which is open and which is positioned adjacent a bottom of the storage chamber;
- a branch line branching communicating with and branching out from an intermediate portion of the first tube segment constituting the venous line;
- a collection container communicating with the branch line and into which the priming solution in the storage chamber is collected by way of the branch line;
- after the priming solution is fed from the priming solution feeding unit to the storage chamber to prime at least the storage chamber, the priming solution in the storage chamber is displaced by blood and is transferred to the collection container due to a difference in height of liquid in the storage chamber relative to liquid in the collection container; and
- height adjusting means for adjusting a height of the collection container.

12. A method of using an extracorporeal circuit comprising:

introducing a priming solution into an extracorporeal circuit, which comprises a blood reservoir, to prime the extracorporeal circuit before introducing a patient's blood into the extracorporeal circuit, the introduction of the priming solution into the extracorporeal circuit introducing the priming solution into an interior of the blood reservoir, the extracorporeal circuit comprising a circuit tube connected to the interior of the blood reservoir, a collection bag, and a branch line having one open end opening into the collection bag and an opposite end connected to and communicating with an intermediate portion of the circuit tube;

positioning the collection bag relative to the blood reservoir so that the one open end is located elevationally lower than a level of the priming solution in the blood reservoir;

permitting the priming solution in the interior of the blood reservoir to flow into the collection bag by way of the branch line under a siphon principle; and closing a clamp on the branch line after priming solution has flowed into the interior of the collection bag to stop the flow of the priming solution from the interior of the blood reservoir to the interior of the collection bag while priming solution remains in the interior of the blood reservoir, cutting the circuit tube to obtain two free ends of the circuit tube, connecting one of the free ends of the circuit tube to an arterial line catheter of a patient, and allowing blood from the patient to flow through a portion of the extracorporeal and enter the blood reservoir at a position elevationally lower than an upper surface of the priming solution remaining in the blood reservoir.

13. The method according to claim 12, further comprising closing a clamp on the branch line while introducing the priming solution into the extracorporeal circuit, and opening the clamp to permit the priming solution in the interior of the blood reservoir to flow into the collection bag by way of the branch line under the siphon principle.

14. The method according to claim 12, wherein the introducing of the priming solution into the extracorporeal circuit comprises introducing the priming solution from a feed bag containing the priming solution directly into the blood reservoir, and then operating a pump forming a part of the extracorporeal circuit to pump the priming solution throughout the extracorporeal circuit.

15. The method according to claim 12, wherein the flow of the priming solution from the interior of the blood reservoir into the interior of the collection bag by way of the branch line automatically ceases when the level of the priming solution in the interior of the blood reservoir is lowered to a level about equal to the elevational position of the one open end of the branch tube.

16. The method according to claim 12, further comprising opening the clamp on the branch line after blood from the patient has entered the blood reservoir to allow additional priming solution from the blood reservoir to flow into the interior of the collection bag.

* * * * *